United States Patent [19]

Siquet-Descans

[11] Patent Number: 5,688,660
[45] Date of Patent: Nov. 18, 1997

US005688660A

[54] METHOD FOR DETERMINING PRODUCT BIODEGRADABILITY

[75] Inventor: Francoise Siquet-Descans, Faimes, Belgium

[73] Assignee: Colgate-Palmolive Company, New York, N.Y.

[21] Appl. No.: 404,690

[22] Filed: Mar. 15, 1995

[51] Int. Cl.⁶ .................................................. C12Q 1/02
[52] U.S. Cl. .......................... 435/29; 435/264; 435/287.5; 436/62; 436/146; 436/149; 205/777.5
[58] Field of Search ............................... 435/29, 287.5, 435/34, 39, 264; 436/133, 148, 146, 149, 150, 62; 205/777.5

[56] References Cited

U.S. PATENT DOCUMENTS

| | | | |
|---|---|---|---|
| 3,660,034 | 5/1972 | Baranyi et al. | 436/20 |
| 3,930,798 | 1/1976 | Schierjott et al. | 23/230 R |
| 4,384,936 | 5/1983 | Obana et al. | 204/403 |
| 4,513,280 | 4/1985 | Hannan et al. | 340/632 |
| 4,898,829 | 2/1990 | Siepmann et al. | 435/289 |
| 4,925,802 | 5/1990 | Nelson et al. | 435/262 |
| 5,068,090 | 11/1991 | Connolly | 422/82.02 |
| 5,079,166 | 1/1992 | Winter et al. | 435/262 |
| 5,094,955 | 3/1992 | Calandra et al. | 435/291 |
| 5,158,662 | 10/1992 | Osborne | 204/403 |
| 5,242,825 | 9/1993 | Mueller et al. | 435/253.3 |
| 5,318,909 | 6/1994 | De Baere | 435/291 |
| 5,425,919 | 6/1995 | Inoue et al. | 436/146 |

FOREIGN PATENT DOCUMENTS

| | | |
|---|---|---|
| 0499302 | 8/1992 | European Pat. Off. . |
| 9527795 | 10/1995 | WIPO . |

OTHER PUBLICATIONS

Soap and Chemical Specialities; Synthetic Detergents Report; pp. 48–52, Nov. 1963.
Soap and Chemical Specialities; Biodegradation of Nonionics; pp. 56–58 and 182; Feb. 1964.
Union Carbide Chemicals for Detergents and Specialties; Tergitols, p. 13; 1965.

*Primary Examiner*—Lien Tran
*Attorney, Agent, or Firm*—Michael J. McGreal

[57] ABSTRACT

A method is directed to a measurement of the biodegradation of a product organic carbon source by the measurement of the change in conductivity of a solution that has absorbed carbon dioxide evolved from the biodegradation of a product organic carbon source. The carbon dioxide that is absorbed is a direct measure of the biodegradability of the organic carbon source.

15 Claims, No Drawings

METHOD FOR DETERMINING PRODUCT BIODEGRADABILITY

BACKGROUND OF THE INVENTION

This invention relates to a method to determine the biodegradability of carbon source products. In particular, the present invention relates to a process where a carbon source product is subject to biodegradation with evolved carbon dioxide absorbed by a solution which changes in conductivity in a known way as a result of carbon dioxide absorption. The change in conductivity consequently is a measure of the extent of biodegradability of the carbon source product.

As a result of new environmental regulations it is necessary to know the biodegradability of a wide range of products. This is particularly the case with regard to various paste and liquid products that are used in the home, office and plant for cleaning purposes. After use these substances go into the municipal waste water system and after treatment flow into a river, lake or other water source. Since these substances must undergo a biodegradation in the waste water treatment system it is valuable to know the biodegradation profile of these products. What is their degradation profile in a waste water treatment system? How quickly is their total organic carbon content (TOC) converted to carbon dioxide and water? This is necessary information in today's regulatory climate.

The testing of products for biodegradability can be accomplished by subjecting a sample of the product to the metabolic action of bacteria and measuring the amount of product before and after testing. Another technique is to subject the product to metabolic action and to measure the evolved carbon dioxide. In this method the evolved carbon dioxide is correlated with the carbon that has been converted to carbon dioxide. However, a better technique has been found. Products can be tested in larger numbers using a shorter period of time for each test. The accuracy remains or is enhanced while the speed of testing is increased. In the formulation of products their biologic degradation properties can be screened while the product formulas are being tested and modified. The effect on the biodegradability of the composition of increasing and/or decreasing components can be quickly determined.

There are wide discrepancies from current methods in the data on the biodegradability of various hydrocarbons as disclosed in the literature. This is interesting since in this literature this is data for a single hydrocarbon. In an analysis of a mixture of hydrocarbons such as in commercial products there would be expected to be a greater discrepancy in the data. In the Zahn-Wellens test for pyridine the percent of biodegradable is 97 percent while in the MITI test it is 15 percent and in the Sturm test 58 percent. This variance is found in the data for the biodegradation of other hydrocarbons. The following Table 1 illustrates that there is not a uniform conformity of results from the various tests for biodegradability. This confirms the need for a standard test which would use known and commercially available test equipment.

TABLE 1

| VARIANCE OF TEST RESULTS (DOC REMOVED) | | | |
|---|---|---|---|
| Compound | Zahn-Wellens Test | MITI Test | Sturm Test |
| N-Methylanaline | 92% | 26% | 92% |
| Pyridine | 97% | 15% | 58% |
| Pentaerythritol | 97% | — | 43% |

TABLE 1-continued

| VARIANCE OF TEST RESULTS (DOC REMOVED) | | | |
|---|---|---|---|
| Compound | Zahn-Wellens Test | MITI Test | Sturm Test |
| 3-Aminobenzoic Acid | 108% | 90% | 97% |
| Adipic Acid | 100% | 96% | 100% |

The Malthus instrument is a known instrument which is used to measure microbiological growth by the detection of changes in conductivity. This can be by a direct technique or an indirect technique. In the direct technique ionized metabolites are released in a culture medium by microbiological metabolism processes. The change in conductivity of the solution due to these ionized metabolites is measured and is a measure of microbiological growth. In the indirect technique evolved carbon dioxide which evolves as a result of microbial metabolism is flowed to and absorbed by a solution of alkali hydroxide. Upon adsorption the alkali hydroxide is converted to alkali carbonate. The conductivity of the alkali hydroxide solution decreases as carbon dioxide is absorbed and alkali carbonate formed. In this instrument, and the attendant process, there is used a microbial culture medium and this medium is placed in an incubator. The microbes are grown in this culture medium and the microbial growth is determined by the direct method or by the indirect method. This is an efficient apparatus and method for microbial growth studies. However, there is not set out any manner for determining the biodegradability of various commercial products using this instrument.

BRIEF SUMMARY OF THE INVENTION

The present invention is directed to a method for determining the biodegradability of organic substances, and in particular product compositions, by monitoring the conductivity change of a solution that absorbs the carbon dioxide that is evolved from the organic substances. In the present method the organic substances are set to the concentration that they would be found when they are disposed of in a municipal waste water treatment system. They are then inoculated with a microbial culture found in a waste water treatment system. The inoculated product solution is then maintained at a given temperature and the evolved carbon dioxide is contacted with an alkali hydroxide solution which absorbs the carbon dioxide and as a result decreases in conductivity. The decrease in conductivity of the solution is proportional to a given amount of carbon dioxide that is absorbed, which in turn correlates with the amount of carbon in the initial product solution that has undergone biodegradation. The decrease in conductivity as a function of the organic carbon that has been converted to carbon dioxide is known from a standard.

The microorganisms that are used are those found in a local waste water treatment system. The use of such a microbial inoculum is the most effective way to evaluate how a product will be degraded in a waste water treatment system. The substance which absorbs carbon dioxide can be any carbon dioxide absorbing substance which will change in conductivity as the carbon dioxide is absorbed. The useful chemically reactive substances include the alkali metal and alkaline earth metal hydroxides, and in particular, sodium hydroxide. When alkali hydroxides are used the carbon dioxide will react with the hydroxides to form carbonates. The carbonates have a lower conductivity than the hydroxide so there will be a decrease in the conductivity of the hydroxide solution as carbon dioxide is evolved and absorbed. This decrease in conductivity correlates to the carbon dioxide evolved which in turn correlates with biodegradation of the carbon source.

DETAILED DESCRIPTION OF THE INVENTION

The present process is directed to relatively quickly measuring the biodegradability of organic carbon containing products in the concentrations in which they enter a municipal waste water system. The objective is to be able to screen product formulations relatively quickly for their biodegradable properties. It is the intent in the development of a product that it be very useful and effective, that it be stable, but yet when it enters into the waste water stream that it be readily biodegradable. In many instances these are competing objectives.

In the present process a product that is used in the home, office or plant is diluted to the concentration in which it would enter the waste water system. It then is inoculated with a culture of microorganisms from a local waste water treatment system and incubated. The product to be biodegraded is then the only organic carbon source. During the incubation carbon dioxide is evolved as the microorganisms metabolize the product containing the organic carbon. This carbon dioxide is contacted with a solution which absorbs carbon dioxide, and which on the absorption of carbon dioxide undergoes a conductivity change. This conductivity change is directly proportional with the amount of evolved carbon dioxide which in turn is in a direct relationship with the biodegradation of the organic carbon containing product.

Essentially, any substance which is at least partially water soluble can be tested as to its biodegradability by this method. This includes detergents, shampoos, soaps, fabric softeners, cleaners, polishes and dentifrices. The biodegradability of a dishwashing detergent or fabric detergent can be quickly determined. During product development the formulations can be quickly checked for biodegradability as the components are adjusted. In this way the use properties of the product, as well as biodegradability, can be optimized.

The microorganisms that are used are predominantly a Pseudomonas sp. This is a species of bacteria that is common in a waste water treatment system. The organisms are collected on a sterilized filter paper (usually a Whatman N° 44) and stored at about 4° C. Generally the number of bacteria in colony forming units (CFU) per milliliter is about $10^4$.

The instrument that preferably is used is a Malthus analyzer. The liquid product sample size is about 1 ml to 4 ml and preferably about 2 ml. The inoculum is added to the liquid product sample. The incubator is maintained at a temperature of about 25° C. The aqueous alkali hydroxide solution will have a concentration of about 0.05N to about 0.5N and preferably about 0.2N. About 0.5 to 2ml of solution is used, and preferably about 1 ml. The evolved carbon dioxide is flowed into this solution. The change in conductivity is measured in microsiemens per hour. The greater the change in conductivity the greater will be the biodegradability of the organic carbon source product.

The change in conductivity is a result of the conversion of alkali hydroxide to alkali carbonate. Sodium hydroxide or potassium hydroxide can be used but with the use of sodium hydroxide being preferred.

The biodegradation is calculated as follows:

$$\% \text{ Biodegradation} = \frac{\Delta Cm}{\Delta CT}$$

where $\Delta Cm$ is the difference in conductivity over a period of 2m hours; $\Delta CT = Kx(Y)$ where $\Delta CT$ is the theoretical conductivity change, K is a cell constant and Y represents the ionic composition of the product to be tested. In operation the curve from an unknown is compared with the curve from a known standard and a percentage biodegradation calculated. In the Malthus analyzer this is done by a computer.

A comparison of the data from this method and data from the literature with regard to the biodegradability of various substances is given in the accompanying Table 2.

TABLE 2

|  | Acid Benzoic | Acid Citric | Dowfax | PnB | DPnB | TPnB |
|---|---|---|---|---|---|---|
| Published Percent | >60 | >60 | 37 | >60 | 46 | 20 |
| Analyzed Percent | 76 | 51 | 12 | 71 | 0 | 0 |

PnB=propylene glycol monobutyl ether
DPnB=dipropylene glycol monobutyl ether
TPnB=tripropylene glycol monobutyl ether
Dowfax=$C_{12-15}$—O—$(CH(CH_3)$—$CH_2$—$O)_{4-5}$—$(CH_2CH_2O)_6H$ The data in this Table 2 provides a good correlation to the published data for the tested materials.

EXAMPLE 1

At the start of an analysis the cell of a Malthus Analyzer is first rinsed with a detergent (Decon from U.K.) at a concentration of 5 percent for about 4 hours and then rinsed with deionized water. This is followed by sterilization at 121° C. for 20 minutes.

2 ml of a benzoic acid sample to be analyzed for biodegradability is added into the sterilized cell and the cell is placed in the Malthus Analyzer. Added to the cell part containing the electrodes is 1 ml of a solution that contains 0.1N sodium hydroxide. The bacteria are added to the organic sample to be tested, which in this case is benzoic acid, and the sample maintained at 25° C. The bacteria are Pseudomonas sp and are in a concentration of about $10^4$ per ml. The cell is maintained at the temperature of 25° C. until the organic carbon that is biodegradable has been converted to carbon dioxide.

The data on the biodegradation of benzoic acid is given in Table 2. Also, in this table is a comparison with the biodegradation tested by the standard method of incubating a hydrocarbon sample of a product with a pseudomonas bacteria and determining the amount of the hydrocarbon remaining at the end of the analysis.

EXAMPLE 2

The procedure of Example 1 was repeated to detect the biodegradation of citric acid, Dowfax, propylene glycol monobutyl ether, dipropylene glycol monobutyl ether and tripropylene glycol monobutyl ether. The results of these tests are set out in Table 2.

EXAMPLE 3

A comparison was made using the procedure of Example 1 and the DOC die-away procedure for the Ajax all purpose cleaner (Denmark), an experimental all purpose cleaner formula, and Vel Ultra light duty detergent (Denmark). In the DOC die-away procedure an inoculum of the bacteria is prepared from a sample from a waste water treatment system. The bacteria concentration is adjusted to $\pm 10^7$ bacteria per ml. A 150 ml sample of the product to be tested is placed in the conical flasks and the bacteria culture added. The solution is aged for at least 28 days at room temperature and with aeration. The solution is measured for dissolved organic carbon content on days 0, 3, 7, 14 and 28. The dissolved organic carbon content can be measured by any of the prior art techniques. Control samples are provided and analyzed to provide baseline data. The percent of biodegradation is calculated from the data on the decrease in the dissolved organic carbon content.

The results are given in Table 3.

TABLE 3

| Product | Percentage of Biodegradation by Present Process | Percentage of Biodegradation by DOC Die-Away Process |
| --- | --- | --- |
| Ajax | 19% | 14% |
| Experimental Formula | 0% | 5% |
| Vel Ultra | 30% | 31% |

It is seen that there is a close comparison of the results by each process.

What is claimed is:

1. A process for determining the biodegradability of an organic carbon source comprising providing a liquid sample of said organic carbon source having a known organic carbon content, diluting said sample to a concentration at which it would enter a waste water system, inoculating said sample with microorganisms obtained from a waste water treatment system, incubating said inoculated sample so that carbon dioxide evolves as said microorganisms metabolize said organic carbon source, contacting the evolved carbon dioxide with a solution which takes up the carbon dioxide and changes its electrical conductivity, measuring the change in conductivity of said solution as carbon dioxide is taken up, and comparing the conductivity of said solution with the conductivity of a known standard to determine the amount of organic carbon contained in said organic carbon source that has been biodegraded by said microorganisms.

2. The process as in claim 1 wherein said organic carbon source is a detergent composition.

3. The process as in claim 1 wherein said organic carbon source is a soap composition.

4. The process as in claim 1 wherein said organic carbon source is a fabric softener.

5. The process as in claim 1 wherein the microorganisms are predominantly Pseudomonas sp.

6. The process as in claim 1 wherein said solution which takes up carbon dioxide contains a substance which reacts with carbon dioxide to form a solution having a decreased conductivity.

7. The process as in claim 6 wherein said substance which reacts with carbon dioxide is an alkali hydroxide.

8. The process as in claim 7 wherein said alkali hydroxide is sodium hydroxide.

9. The process as in claim 7 wherein said alkali hydroxide is potassium hydroxide.

10. A process for determining the biodegradability of an organic carbon source which is a household cleaning product comprising providing a liquid sample of said organic carbon source and having a known carbon content, diluting said sample to a concentration at which it would enter a waste system, inoculating said sample with microorganisms which are predominately Pseudomonas Sp and which are collected from a waste water treatment system, inubating said inoculated sample so that said microorganisms metabolize said organic carbon source, contacting the evolved carbon dioxide with an alkali hydroxide solution which reacts with the carbon dioxide and changes its electrical conductivity, measuring the change in conductivity of said solution as carbon dioxide is removed; and comparing the conductivity of said solution with the conductivity of a known standard to determine the amount of organic carbon contained in said organic carbon source that has been biodegraded by said microorganisms.

11. The process as in claim 10 wherein said organic carbon source is a detergent composition.

12. The process as in claim 10 wherein said organic carbon source is a soap composition.

13. The process as in claim 10 wherein said organic carbon source is a fabric softener.

14. The process as in claim 10 wherein said alkali hydroxide is sodium hydroxide.

15. The process as in claim 10 wherein said alkali hydroxide is potassium hydroxide.

* * * * *